United States Patent [19]

Murata et al.

[11] 4,188,498

[45] * Feb. 12, 1980

[54] PROCESS FOR PRODUCING LINALOOL

[75] Inventors: Atsuo Murata; Shuji Tsuchiya; Hideo Suzuki; Hisao Ikeda, all of Funabashi, Japan

[73] Assignee: Nissan Chemical Industries, Ltd., Tokyo, Japan

[*] Notice: The portion of the term of this patent subsequent to Aug. 15, 1995, has been disclaimed.

[21] Appl. No.: 902,753

[22] Filed: May 3, 1978

[30] Foreign Application Priority Data

May 18, 1977 [JP] Japan .................................. 52-57385

[51] Int. Cl.² ........................................... C07C 33/02
[52] U.S. Cl. .................................................. 568/875
[58] Field of Search ......................................... 568/875

[56] References Cited

U.S. PATENT DOCUMENTS

| 2,604,455 | 7/1952 | Reynolds et al. ..................... 252/412 |
| 4,107,219 | 8/1978 | Murata et al. ........................ 568/875 |

FOREIGN PATENT DOCUMENTS 2720839  11/1977  Fed. Rep. of Germany ........... 568/875

Primary Examiner—Joseph E. Evans
Attorney, Agent, or Firm—Oblon, Fisher, Spivak, McClelland & Maier

[57] ABSTRACT

Linalool is produced by a hydrogenation of O-linalyl-N,N-dimethyl hydroxylamine having the formula

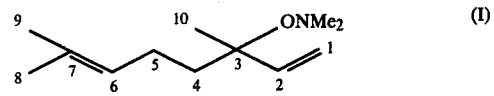

wherein Me represents methyl group and the reference numerals 1 to 10 represent 1 to 10 carbon positions under a hydrogen partial pressure of lower than 30 Kg/cm² in the presence of a catalyst of a combination of Ni or Co component with a modifying component selected from the group consisting of Al, Ge, Sn, As, Sb, S, Se and Cr.

10 Claims, No Drawings

PROCESS FOR PRODUCING LINALOOL

BACKGROUND OF THE INVENTION

The present invention relates to a novel process for producing linalool. More particularly, it relates to a process for producing linalool by a hydrogenation of O-linalyl-N,N-dimethyl hydroxylamine in the presence of the specific catalyst.

Linalool is the useful compound as the starting material for producing vitamins.

The starting material O-linalyl-N,N-deimethyl hydroxylamine can be easily economically produced by a telomerization of isoprene and dimethylamine and a reaction of the resulting nerylamine with hydrogen peroxide and a thermal rearrangement of the resulting nerylamine oxide.

It has been known that linalool is produced by a reduction of O-linalyl-N,N-dimethyl hydroxylamine with zinc and acetic acid. However, an industrially advantageous hydrogenation has not been known.

The inventors have studied to carry out the hydrogenation of O-linalyl-N,N-dimethyl hydroxylamine in the presence of a catalyst of nickel, cobalt or copper whereby dihydrolinalool is obtained. The inventors further studied to carry out the hydrogenation of O-1,2-dihydrolinalyl-N,N-dialkyl hydroxylamine in the presence of a catalyst of copper chromite whereby dihydrolinalool is obtained in high yield.

However, it has been impossible to obtain linalool by a hydrogenation with a catalyst because the double bond between carbon atoms at 1- and 2-positions of O-linalyl-N,N-dimethyl hydroxylamine is easily hydrogenated, though linalool is quite important.

SUMMARY OF THE INVENTION

It is an object of the present invention to provide a process for producing linalool by a hydrogenation which is industrial and economical.

The foregoing and other objects of the present invention have been attained by a hydrogenation of O-linalyl-N,N-dimethyl hydroxylamine in the presence of a combined catalyst of nickel or cobalt component with a modifying component selected from the group of Al, Ge, Sn, As, Sb, S, Se or Cr.

DETAILED DESCRIPTION OF THE PREFERRED EMBODIMENT

The feature of the present invention is to selectively obtain linalool by a hydrogenation of O-linalyl-N,N-dimethyl hydroxylamine in the presence of the specific combined catalyst of nickel or cobalt component with a modifying component of Al, Ge, Sn, As, Sb, S, Se or Cr though linalool could not be obtained by a hydrogenation in the presence of a nickel or cobalt catalyst.

The modifying component may be in a form of alloy or oxide thereof as well as a simple mixed element.

The combination of the nickel or cobalt component with the modifying component is the special combination. In general, elements in the same group of the periodic table impart similar chemical characteristics in a combination. The modifying components are included in the groups 3a, 4a, 5a, 6a, and 6b of the periodic table, however only certain elements impart the effect of the present invention. For example, only aluminum component is effective in the 3a group and linalool can be obtained in high yield by using the Ni-Al, or Co-Al catalyst.

However, if a combination of Ni or Co with B, Ga or In is used as the catalyst, linalool is not substantially obtained.

Only germanium or tin component is effective in the 4a group. However, if a catalyst of Ni-Pb or Co-Pb is used, only a small amount of linalool is obtained.

Only arsenic or antimony component is effective in the 5a group and only sulfur or selenium component is effective in the 6a group and only chromium component is effective in the 6b group. However, the other element components in these group of the periodic table are not effective as the modifying component to combine with nickel or cobalt component.

The catalysts used in the present invention are combination of nickel or cobalt component with a modifying component of Al, Ge, Sn, As, Sb, S, Se or Cr. Two or more modifying component can be combined with nickel or cobalt component and both of nickel and cobalt component can be used with the modifying component.

The molar ratio of the modifying component to the nickel or cobalt component is usually 0.02 to 2 preferably 0.05 to 0.5 as atomic ratio.

When the molar ratio is less than 0.02, the hydrogenation of the double bond is performed whereas when the molar ratio is more than 2, the reduction of the hydroxylamine group is not satisfactory whereby the yield of linalool is too low.

These catalysts can be prepared as follows.

When a modifying component is the component of Al, Ge, Sn, As, Sb or Cr, the nitrate of the modifying component of Al, Ge, Sn As, Sb or Cr as well as nickel nitrate or cobalt nitrate are supported on suitable carrier and the carrier supporting them is calcined and reduced to obtain the catalyst.

Suitable salt of the modifying component and nickel salt or cobalt salt are converted into hydroxides or carbonates thereof by adding a base of ammonia, sodium carbonate etc. in a form of aqueous solution, and the hydroxides or carbonates are supported on a suitable carrier and the carrier supporting them is calcined and reduced to obtain the catalyst.

In general, the latter is preferable.

When a modifying component of non-metal of S, Se or As is used, nickel or cobalt hydroxide or carbonate obtained by adding a base to an aqueous solution of nickel salt or cobalt salt, is supported on a carrier and then, an aqueous solution of a compound having S, Se or As such as $(NH_4)_2SO_4$, $H_2SeO_4$ and $H_3AsO_4$ is added to the carrier and concentrated to dry it and the carrier supporting them is calcined and reduced to obtain the catalyst.

It is also possible to heat the reduced nickel or cobalt catalyst at 200° to 300° C. under passing $H_2S$ or $H_2Se$ to obtain the catalyst.

Suitable carriers include diatomaceous earth, silica-gel, silica-alumina active carbon and other carriers used for supporting a catalytic component. A ratio of the catalytic component of Ni and Co to the carrier is usually in a range of 1 to 60%. The catalytic component can be used without a carrier.

The hydrogenation of O-linalyl-N,N-dimethyl hydroxylamine is carried out under a hydrogen partial pressure of lower than 30 $Kg/cm^2$ preferably 10 to 0.05 $Kg/cm^2$, especially 2 to 0.1 $Kg/cm^2$. When the hydrogen pressure is higher than 30 Kg/cm$^2$, the production of by-products such as dihydrolinalool is highly caused.

When the catalyst of cobalt component and the modifying component is used linalool can be obtained even though the hydrogen pressure is higher than 30 Kg/cm$^2$. However, the yield is not high. When the catalyst of nickel component and the modifying component is used, the hydroxylamine group can be highly reduced, however, the double bonds are also easily hydrogenated. Accordingly, it is preferable to be lower hydrogen pressure especially lower than 2 Kg/cm$^2$.

The temperature in the hydrogenation is higher than room temperature and preferably 50° to 120° C. The velocity of formation of linalool is slow at lower than 50° C. whereas the decomposition is caused to produce small amount of linalool at higher than 120° C.

It is important to use as the starting material O-linalyl-N,N-dimethyl hydroxylamine, since linalool could not be obtained in high yield by the hydrogenation when starting materials having alkyl groups other than dimethyl groups such as O-linalyl-N,N-diethyl hydroxylamine or O-linalyl-N,N-dipropyl hydroxylamine are used.

In the hydrogenation of O-linalyl-N,N-dimethyl hydroxylamine, the amount of the catalyst to the starting material is usually 5 to 3000%. It is preferable to use a large amount of the catalyst.

The hydrogenation can be attained without a solvent. However, it is preferable to dilute O-linalyl-N,N-dimethyl hydroxylamine with an inert solvent such as aliphatic alcohols, ethers, aromatic alcohols, alicyclic alcohols, aromatic hydrocarbons and aliphatic hydrocarbons.

It is preferable to select the solvent so as to be easily separable from the product of linalool.

When linalool is produced by the hydrogenation of O-linalyl-N,N-dimethyl hydroxylamine, a small amount of dihydrolinalool is also produced. Dihydrolinalool can be separated by distillation after the separation of the catalyst.

The present invention will be further illustrated by certain examples and references.

EXAMPLE 1

A mixture of 5.6 g of silica gel with an aqueous solution prepared by dissolving 18 g of Ni(NO$_3$)$_2$.6H$_2$O and 1.5 g of SnCl$_2$.2H$_2$O in 100 ml of water, was stirred and an aqueous solution prepared by dissolving 6 g of sodium carbonate in 40 ml of water was added dropwise to the mixture to give pH of 8 to 9. The mixture was further stirred and then, kept in stand-still for one night. The precipitate was filtered and washed with water and dried at 110° C. for 10 hours. A catalyst was prepared by reducing 6 g of the dried powder at 500° C. for 2 hours in hydrogen gas flow. The catalyst contained the components at ratios of Ni:Sn:Silica gel of 36:8:56 by weight.

The catalyst was charged in a reactor and 6 g of O-linalyl-N,N'-dimethyl hydroxylamine and 30 g of ethanol were further charged and hydrogen was fed into the reactor under stirring at 77° C. for 40 minutes to perform the hydrogenation. After the hydrogenation, the mixture was cooled to the room temperature and the catalyst was separated by a filtration.

The reaction mixture was analyzed by the gas chromatography to find an 87% conversion, 39% yield of linalool and 7% of yield dihydrolinalool.

EXAMPLE 2

In accordance with the process of Example 1 a catalyst was prepared except using 11 g of Ni(NO$_3$)$_2$.6H$_2$O and 4.2 g of Sn Cl$_2$.2H$_2$O to contain the components at ratios of Ni:Sn:Silica gel of 22:22:56 by weight and the hydrogenation was carried out except using 3 g of O-linalyl-N,N-dimethyl hydroxylamine and reacting one hour.

As the result, the conversion was 71%, the yield of linalool was 26% and the yield of dihydrolinalool was 3.5%.

REFERENCE 1

In accordance with the process of Example 1 except using O-linalyl-N,N-diethyl hydroxylamine instead of O-linalyl-N,N-dimethyl hydroxylamine, the hydrogenation was carried out.

As the result, the conversion was 100%, however, linalool was not obtained and only decomposed products were obtained.

EXAMPLE 4

In accordance with the process of Example 2, a catalyst was prepared except using 20 g of Co(NO$_3$)$_2$.6H$_2$O and 0.76 g of SnCl$_2$.2H$_2$O to contain the components at ratios Co:Sn:Silica gel of 40:4:56 by weight, and the hydrogenation was carried out except using 0.4 g of O-linalyl-N,N-dimethyl hydroxylamine.

As the result, the conversion was 89%, the yield of linalool was 65% and the yield of dihydrolinaolool was 4%.

The hydrogenation of O-linalyl-N,N-dimethyl hydroxylamine was repeated by using the same catalyst. The catalytic activity of the catalyst was not decreased.

EXAMPLE 5

In accordance with the process of Example 4 except using 1 g of O-linalyl-N,N-dimethyl hydroxylamine and the conditions of the reaction temperature of 100° C. and the hydrogen pressure of 15 Kg/cm$^2$ and the reaction time of 30 minutes, the hydrogenation was carried out.

As the result, the conversion was 75%, the yield of linalool was 25% and the yield of dihydrolinalool was 16%.

REFERENCE 2

In accordance with the process of Example 5, except using the condition of the reaction temperature of 125° C., the hydrogenation was carried out.

As the result, the conversion was 100%, however, linalool was not obtained and only decomposed products were obtained.

REFERENCE 3

In accordance with the process of Example 5 except using the condition of hydrogen pressure of 40 Kg/cm$^2$, the hydrogenation was carried out.

As the result, the conversion was 87%, the yield of linalool was 9% and the yield of dihydrolinalool was 29%.

EXAMPLE 6

In accordance with the process of Example 1 except varying the amount of Ni(NO$_3$)$_2$.6H$_2$O or Co(NO$_3$)$_2$.6H$_2$O and varying the kind and the amount of the modifying component, the catalysts of Ni-Cr, Ni-Al, Ni-Ge, Ni-Sb and Co-Cr were prepared.

In order to provide the modifying components, each nitrate was used for Al or Cr component and each chloride was used for Ge or Sb component.

The catalyst was prepared to give 56% by weight of silica gel and a total of the Ni or Co component and the modifying component as metal of 44% by weight.

In accordance with the process of Example 1 except using 1.5 to 6 g of O-linalyl-N,N-dimethyl hydroxylamine in the case of the Ni type catalyst and 0.4 g of O-linalyl-N,N-dimethyl hydroxylamine in the case of the cobalt type catalyst, and varying the amount of the catalyst and the reaction time, the hydrogenations were carried out.

The results are shown in Table 1.

Table 1

| Test No. | 1 | 2 | 3 | 4 | 5 |
|---|---|---|---|---|---|
| Catalyst |  |  |  |  |  |
| Components | Ni-Cr | Ni-Al | Ni-Ge | Ni-Sb | Co-Cr |
| ratio (wt. %) | 36:8 | 40:4 | 42:2 | 36:8 | 36:8 |
| Amount Cat/Start, material | 2 | 4 | 1 | 1 | 15 |
| Reaction time (min.) | 35 | 10 | 10 | 10 | 120 |
| Conversion (%) | 65 | 86 | 72 | 80 | 88 |
| Yield |  |  |  |  |  |
| Linalool (%) | 20 | 32 | 24 | 20 | 64 |
| Dihydrolinalool (%) | 16 | 17 | 19 | 14 | 4 |

EXAMPLE 7

A mixture of 5.6 g of silica gel with an aqueous solution prepared by dissolving 21 g of Ni(NO$_3$)$_2$.6H$_2$O in 100 ml of water and an aqueous solution prepared by dissolving 6 g of ammonium carbonate in 40 ml of water was added dropwise to the mixture to give pH of 8 to 9. The mixture was further stirred and then kept in standstill for one day. The precipitate was filtered and washed with water and dipped in an aqueous solution prepared by dissolving 0.83 g of (NH$_4$)$_2$SO$_4$ in 30 ml of water for one day. The mixture was concentrated on a hot water bath and dried at 110° C. for 10 hours and reduced at 500° C. for 2 hours in hydrogen gas flow.

The catalyst contained the components at ratios of Ni:S:Silica gel of 42:2:56.

In accordance with the process of Example 1 except using 8 g of the catalyst and 2 g of O-linalyl-N,N-dimethyl hydroxylamine and the condition of the reaction time of 55 minutes, the hydrogenation was carried out. As the result, the conversion was 95%, the yield of linalool was 33% and the yield of dihydrolinalool was 2%.

EXAMPLE 8

In accordance with the process of Example 7 except using H$_2$SeO$_3$ for the Se component and H$_3$AsO$_4$ for the As component and varying the amount of Ni(NO$_3$)$_2$ or Co(NO$_3$)$_2$.6H$_2$O and varying the kind and the amount of the modifying component, the catalysts of Ni-As, Ni-Se, Co-As, Co-S and Co-Se were prepared.

In accordance with the process of Example 6 except using the catalysts, the hydrogenations of O-linalyl-N,N-dimethyl hydroxylamine were carried out. The results are shown in Table 2.

Table 2

| Test No. | 6 | 7 | 8 | 9 | 10 | 11 | 12 |
|---|---|---|---|---|---|---|---|
| Catalyst |  |  |  |  |  |  |  |
| Components | Ni-As | Ni-Se | Co-As | Co-As | Co-S | Co-Se | Co-As |
| ratio (wt. %) | 36:8 | 42:2 | 40:4 | 36:8 | 42:2 | 40:4 | 38:6 |
| Amount Cat/Start, material | 1 | 1 | 15 | 2 | 15 | 15 | 2 |
| Reaction time (min.) | 20 | 60 | 15 | 450 | 33 | 120 | 220 |
| Conversion (%) | 68 | 72 | 95 | 88 | 85 | 87 | 94 |
| Yield |  |  |  |  |  |  |  |
| Linalool (%) | 14 | 22 | 74 | 63 | 61 | 65 | 72 |
| Dihydrolinalool (%) | 18 | 9 | 0 | 0 | 10 | 2 | 2 |

In Test No. 12, the hydrogen pressure was 1 Kg/cm$^2$, and methanol was used as the solvent and the hydrogenation was carried out at 60° C.

EXAMPLE 9

In accordance with the process of Example 1 except using 40 g of Ni(NO$_3$)$_2$.6H$_2$O and 1.5 g of SnCl$_2$.2H$_2$O without a carrier, the catalyst of Ni-Sn having a ratio of Na-Sn of 91:9 was prepared.

In accordance with the process of Example 1, the hydrogenation of O-linalyl-N,N'-dimethyl hydroxlamine was carried out for 25 minutes. As the result, the conversion was 52%, the yield of linalool was 23% and the yield of dihydrolinalool was 7%.

What is claimed is:

1. A process for producing linalool which comprises hydrogenating O-linalyl-N,N-dimethyl hydroxylamine having the formula

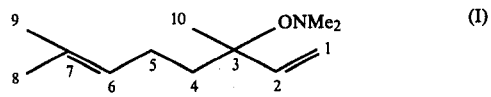 (I)

wherein Me represents a methyl group and the reference numerals 1 to 10 represent 1 to 10 carbon positions, under a hydrogen partial pressure of lower than 30 kg/cm$^2$ in the presence of a catalyst which is a combination of a first component selected from the group consisting of Ni, Co and mixtures thereof with a modifying component selected from the group consisting of Al, Ge, Sn, As, Sb, S, Se and Cr.

2. A process according to claim 1 wherein the atomic ratio of the modifying component to the component selected from the group consisting of Ni and Co, and mixtures thereof is 0.02 to 2.

3. A process according to claim 1 wherein the component selected from the group consisting of Ni Co, and mixtures thereof is in metallic form and the modifying component is in a form of metal or oxide thereof.

4. A process according to claim 1 wherein the hydrogenation is carried out in an inert solvent.

5. A process according to claim 1 wherein the component selected from the group consisting of Ni, Co, and mixtures thereof and the modifying component are supported on a carrier.

6. A process according to claim 1 wherein the hydrogenation is carried out at a temperature of 50° to 120° C.

7. The process of claim 2 wherein said atomic ratio is 0.05 to 0.5.

8. The process of claim 5 wherein said carrier is selected from the group consisting of diatomaceous earth, silica gel, silica-alumina, active carbon and mixtures thereof.

9. The process of claim 1 wherein the partial pressure of said hydrogen is 0.05 to 10 kg/cm².

10. The process of claim 9 wherein said pressure is 0.1 to 2 kg/cm².

* * * * *